United States Patent [19]

Grayson

[11] Patent Number: 4,487,327

[45] Date of Patent: Dec. 11, 1984

[54] LOCKING CAPSULE

[76] Inventor: Robert E. Grayson, Rte. 2 S. Box 2186, Great Falls, Mont. 59401

[21] Appl. No.: 451,844

[22] Filed: Dec. 21, 1982

[51] Int. Cl.³ .............................................. A61B 19/02

[52] U.S. Cl. ........................................ 220/8; 220/306; 206/530

[58] Field of Search ........................... 220/8, 4 B, 306; 206/528, 530

[56] References Cited

U.S. PATENT DOCUMENTS

| | | | |
|---|---|---|---|
| 2,718,980 | 9/1955 | Strom | 220/306 |
| 3,198,375 | 8/1965 | Hunter | 220/306 |
| 3,399,803 | 9/1968 | Ogleyee et al. | 220/306 |
| 3,508,678 | 4/1970 | Graham et al. | 220/306 |
| 4,040,536 | 8/1977 | Schwarz | 220/8 |

*Primary Examiner*—Steven M. Pollard

*Attorney, Agent, or Firm*—Matthew L. Ajeman

[57] ABSTRACT

Capsules (10) such as used for administering medicines, foods, and the like, are formed by a pair of sections (12, 14) locked to one another by a latching assembly (28) including a projecting member (30) provided on one of the sections and a keeper or abutment (34) provided on the other of the sections. By this arrangement, the projecting member and the abutment will snap together when the associated sections are matingly joined so as to resist separation.

14 Claims, 15 Drawing Figures

LOCKING CAPSULE

BACKGROUND OF THE INVENTION

1. Field of the Invention

This invention relates generally to edible capsules such as used for dispensing medicines, foods, and the like, and particularly to such a capsule in which the sections thereof lock together in a secure manner, so as to prevent accidental loss of the contents of the capsule, tampering, and the like.

2. Description of the Prior Art

It is well known to put medicines, foods, and the like, into capsules fabricated from a material which is digestable and not toxic to a person's body. In general, these capsules are constructed in the form of a pair of generally symmetrical sections of cylindrical cross section, hollow with one open end and one closed end, and joinable or mateable at the open ends thereof. A basic disadvantage associated with this construction is that the capsule sections, which generally are constructed from a biodegradable, digestible, synthetic resin, and the like, have smooth inner and outer surfaces which tend to slide relative to one another, with the result that the capsules sometimes fall open spilling their contents. In any event, and more importantly, it is very easy to pull apart a capsule, discharge the contents therein, and subsequently refill the capsule sections with a foreign substance prior to placing the sections back together again. This can be done without any evidence of tampering from a visual examination of the capsule.

Accordingly, there is a need for a technique for constructing such capsules in a manner wherein they do not readily come apart once joined, so as to prevent accidental spillage and tampering with them. In particular, there is a need for internally digestable capsules which cannot be opened and reassembled without signs of same.

Summary of the Invention

It is an object of the present invention to provide an edible capsule the sections forming which are locked together in a secure manner.

It is another object of the present invention to provide a locking assembly suitable for use with capsules containing medicines, foods, and the like.

Still another object of the present invention is to provide a latching arrangement for mating sections of a capsule which resists release and separation of previously latched capsule sections without evidence of such release and reengagement.

These and other objects are achieved according to the present invention by providing a locking apparatus for use with a capsule to be used for internal consumption, comprising a hollow first section having an open end and a closed end, a hollow second section also having an open end and a closed end and mateable at the open end thereof with the first section at the open end thereof to form an enclosure, and a latching assembly associated with each of the first section and the second section for locking the sections to one another.

The locking or latching assembly preferably includes a projecting member provided on the first section, and an abutment provided on the second section and arranged for lockingly engaging the projecting member so as to secure the first section and the second section to one another.

The projecting member and abutment can take various forms, but usually are in the basic configuration of an annular flange and cooperating annular ring. If desired, so as to increase the grip of the assembly, a plurality of side-by-side rings can be provided extending from an open end to a closed end of an associated capsule section.

Advantageously, one of these sections is longer than the other, with the locking part associated therewith set back so as to form a stabilizing collar where the sections join together.

DESCRIPTION OF THE PREFERRED EMBODIMENTS

Figure 1:
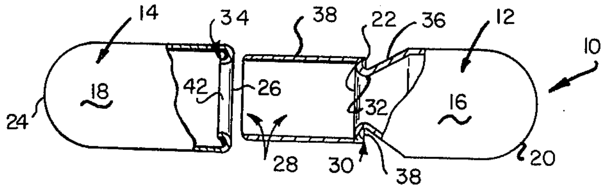
FIG. 1 is an exploded, side elevational view, partly cut away and in section, showing a first embodiment of the present invention.
Figure 2:
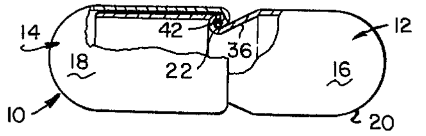
FIG. 2 is a side elevational view, partly cut away and in section showing the embodiment of the invention illustrated in FIG. 1, but in an assembled mode.

Referring now more particularly to FIGS. 1 and 2 of the drawing, there is illustrated a capsule 10 according to the present invention constructed from an edible and digestable material as is conventional, and including a first section 12 and a second section 14 each comprising a generally cylindrical, hollow body 16 and 18, respectively. Each body 16, 18, has a pair of spaced ends, one of the ends 20, 24 being closed and the other of the ends 22, 26 being open. Each of the sections 12, 14 is joinable to the other of the sections 14, 12 at the open end 22, 26 thereof to form an enclosure. Associated with the sections 12 and 14 is a latching assembly 28 according to the present invention, and to be described in detail below, for locking section 12 to section 14 and preventing tampering with a capsule 10.

Latching assembly 28 includes a projecting member 30 provided on section 12 and comprising an annular flange 32 in the embodiment of FIGS. 1 and 2, as well as an abutment 34 provided on section 14 and arranged for lockingly engaging member 30. More specifically, section 12 has displaced from the open end 22 thereof a recessed or reduced diameter portion 36 extending inwardly of that section. Portion 36 terminates in an annular flange 32 as discussed above and which can be described as an open one-half of a torus that in turn forms an annulus facing the closed end 20 of section 12. As can be seen, the annular flange 32 is disposed rearwardly of open end 22 of body 16, toward closed end 20, so as to form a sleeve 38 which penetrates into the hollow interior of body 18 a sufficient distance to provide a junction between sections 12 and 14 which resists bending moments, and the like. Abutment 34 provided on body 18 extends inwardly of section 14 and retainingly engages with flange 32 to lock the sections 12 and 14 relative to one another. This abutment 34 comprises an anchor ring 40 arranged extending inwardly from an outer surface of body 18 and opening toward the closed end 24 of section 14. Further, anchor ring 40 is arranged for lockingly engaging with the one-half of a torus of projecting member 30, with the outer surface of each of the first section 12 and the second section 14 being cylindrical and of substantially equal diameters for matingly engaging one another. By proper dimensions, sleeve 38 will then slide snugly into the interior of body 18 to obtain the result referred to above.

Once locked in place as seen in FIG. 2, it will be appreciated that it will be difficult to unlock the sections 12, 14 from one another without damaging the body 16, 18 so as to show outward signs of tampering.

Several additional embodiments of the present invention will be described below, with in each instance like parts to those designated in FIGS. 1 and 2 being given the same reference numeral with a suitable prefix added to the numeral.

Figure 3:
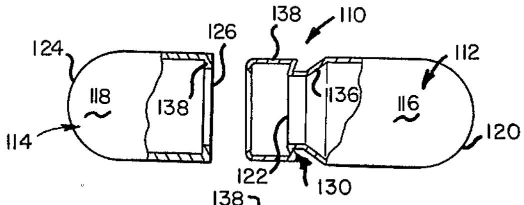
FIG. 3 is an exploded, side elevational view, partly cut away and in section, showing a second embodiment of a locking capsule according to the present invention.
Figure 4:
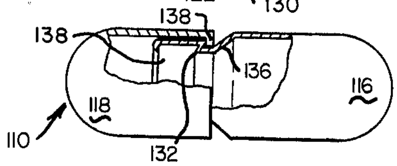
FIG. 4 is a side elevational view, partly cut away and in section, showing the embodiment of FIG. 1, but in an assembled mode.

Referring now to FIGS. 3 and 4 of the drawing, a capsule 110 according to the present invention includes a first section 112 and a second section 114 each comprising a respective body 116, 118 having associated therewith the closed ends 120 and 124 and the open ends 122 and 126. Provided on sections 112 and 114 is a latching assembly 128 including a projecting member 130 in the form of an annular flange 132 which simply flares rearwardly toward closed end 120 and is selectively engageable with an abutment 134 to lockingly join sections 112 and 114 as seen in FIG. 4. Preferably, body 116 of section 112 is provided with a recessed portion 136 similar to section 36 and forming a sleeve 138 slidably insertable into the interior of body 118 to function in a manner similar to that of sleeve 38. Abutment 134 comprises an anchor ring 140 arranged extending inwardly from an outer surface of section 114 so as to lockingly engage with projecting member 130 as locked in behind abutment 134, the sections 112 and 114 will be securely fastened to one another.

Figure 5A:
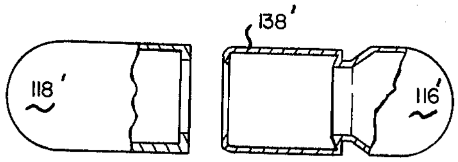
FIG. 5A is a side elevational view, partly cut away and in section, showing a modification of the embodiment shown in FIGS. 3 and 4.
Figure 5B:
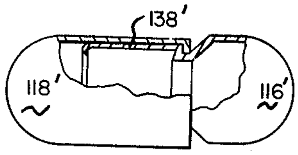
FIG. 5B is a side elevational view, partly cut away and in section, showing the embodiment of FIG. 5A, but in an assembled mode.

FIG. 5A and 5B shows a modification of the embodiment of FIGS. 3 and 4 wherein a sleeve 138' is elongated relative to sleeve 138. The outward ends of both sleeve 138 and 138' preferably are curved as shown to insertion of an associated section 116, 116' into a short section 118, 118' , respectively.

Figure 6:
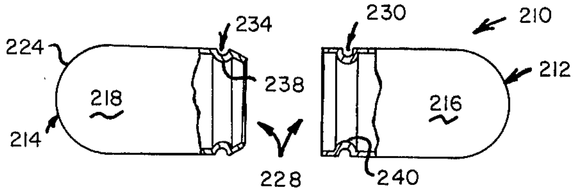
FIG. 6 is an exploded, side elevational view, partly cut away and in section, showing a third embodiment of a locking capsule according to the present invention.

FIG. 6 shows an embodiment of the present invention in which a capsule 210 includes a first section 212 and a second section 214 each including a respective body 216 and 218 provided with the usual closed ends 220 and 224, and opened ends 222 and 226. A latching assembly 228 associated with section 212 and 214 includes a projecting member 230 in the form of an outwardly open annular flange 232 which cooperates with an abutment 234 provided on section 214. The outer end of abutment 234 is curved inwardly of body 218 so as to form a flared flange 238 arranged for assisting insertion of section 214 into section 212. Abutment 234 is an anchor ring 240 opening outwardly and having a cross section similar to member 230 for matingly engaging therewith.

Figure 7:
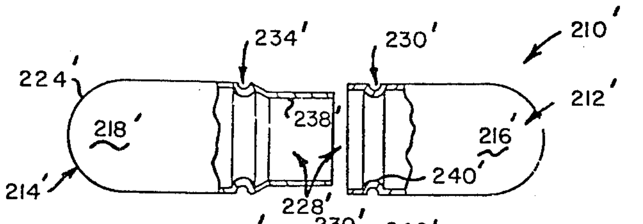
FIG. 7 is a side elevational view, partly cut away and in section, showing the embodiment illustrated in FIG. 6, but in an assembled mode.
Figure 8:
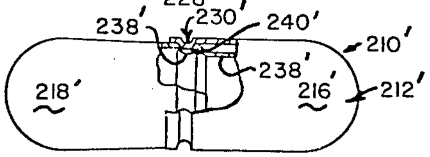
FIG. 8 is a side elevational view, partly cut away and in section, showing a modification of the embodiment shown in FIGS. 4 and 5.

FIGS. 7 and 8 shows a modification of the embodiment of FIG. 6, wherein a capsule 210' each including a respective body 216 and 218' provided with the usual closed ends 220 and 224, and open ends 222 and 226'. The latching assembly 228 associated with section 212' and 214' includes a projecting member 230 in the form of an outwardly open annular flange 232 which cooperates with an abutment 234 provided on section 214'. Abutment 234 is set toward end 224 from end 226 so as to form a sleeve 238 insertable into body 218. Abutment 234 is in the form of an anchor ring 240 also opening outwardly so that projecting member 230 and abutment 234 have a cross section similar to the other and are arranged for matingly engaging with one another in the manner shown. More specifically, in the embodiments illustrated in FIGS. 6, 7 and 8, the cross section of each of the abutment 234 and the projecting member 230 generally is semicircular.

Figure 9:
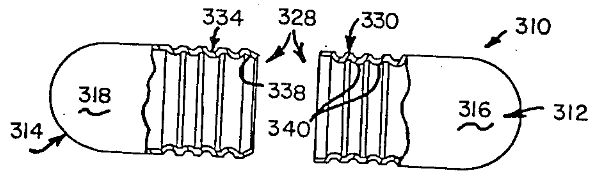
FIG. 9 is an exploded, side elevational view, partly cut away and in section, showing a fourth embodiment of a locking capsule according to the present invention.
Figure 10:
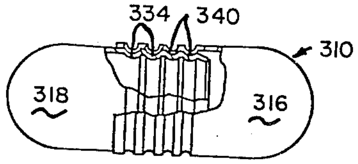
FIG. 10 is a side elevational view, partly cut away and in section, showing the embodiment of FIG. 9, but in an assembled mode.

A variation of the embodiment shown in FIGS. 7 and 8 is illustrated in FIGS. 9 and 10, wherein a capsule 310 includes a first section 312 and a second section 314 each having a respective body 316 and 318, and the usual closed ends 320 and 324 and open ends 322 and 326. A latching assembly 328 is similar to that of FIGS. 7 and 8, as mentioned above, except that there are a plurality of projecting member 330 each in the form of an outwardly directed annular flange 332 and which engage with an abutment 334. A curve of the end one of the abutment 334 forms a flange 338 on section 314, which flange 338 functions to help guide section 314 into section 312. Abutment 334 preferably includes a plurality of anchor rings 340 each similar to rings 240 and arranged for engaging the respective one of the projecting member 330. This embodiment functions similar to that of FIGS. 7 and 8, except that the plurality of side-by-side projecting members and cooperating anchor rings will increase the strength of the connection.

Figure 11:
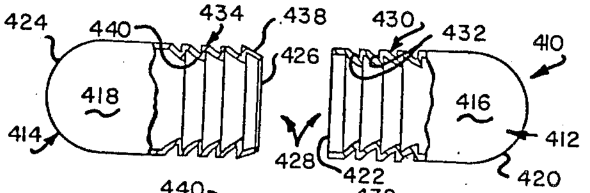
FIG. 11 is an exploded, side elevational view, partly cut away and in section, showing a still further embodiment of a locking capsule according to the present invention.
Figure 12:
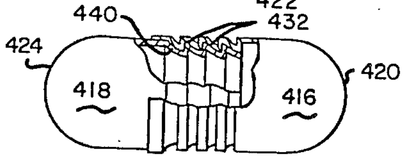
FIG. 12 is a side elevational view, partly cut away and in section, showing the embodiment of FIG. 11, but in an assembled mode.

A capsule 410 according to the present invention is illustrated in FIGS. 11 and 12 of the drawing as including a first section 412 and a second section 414 each comprising a body 416 and 418, respectively, and the usual closed ends 420 and 424 and open ends 422 and 426. A latching arrangement 428 is similar to arrangement 328, except that the plurality of projecting members 430 is each in the form of an annular flange 432 having a saw-tooth shape in cross section. Similarly, an abutment 434, flared toward open end 426 to form a flange 438 similar to flange 338, is in the form of a plurality of anchor rings 440 each also having the aforementioned saw-tooth configuration in section. Thus, it can be seen that capsule 410 is similar to capsule 310, except that latching assembly 428 is designed toward more positive engagement between the projecting members and associated anchor rings.

Figure 13:
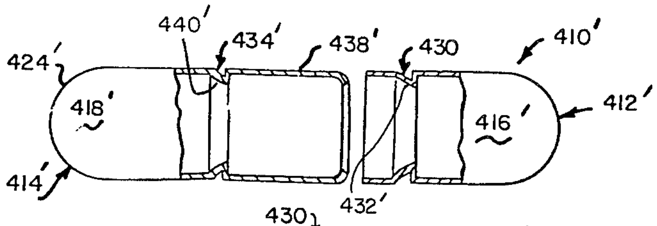
FIG. 13 is a side elevational view, partly cut away and in section, showing still another embodiment of the invention.
Figure 14:
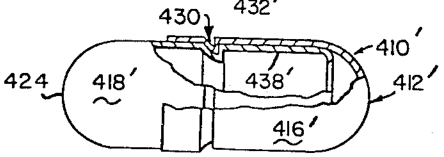
FIG. 14 is a side elevational view, partly cut away and in section, showing the embodiment of FIG. 13, but in an assembled mode.

FIGS. 13 and 14 illustrate an embodiment with a short section 416' similar to section 416, but with only a single lock ring flange 432' arranged for engaging a saw-tooth anchor ring 440'.Other similar parts to the embodiment of FIGS. 11 and 12 are given the same reference numeral as in FIGS. 11 and 12, but primed. Note the elongated sleeve 438' similar to sleeves 138' and 238'.

As can be readily understood from the above description and from the drawings, a locking capsule according to the present invention not only will virtually eliminate accidental spillage of the contents of a medicinal, dietary, or other similar capsule, but will discourage tampering with the capsule. Even in the event one succeeded in opening the capsule, the sections of the capsule would have been so misformed and mutilated that even a casual observer would see external signs of such tampering.

While the principles of the invention have now been made clear in illustrated embodiments, there will be immediately obvious to those skilled in the art, many modifications of structure, arrangements, proportions, the elements, materials, and components used in the practice of the invention, and otherwise, which are particularly adapted for specific environments and operation requirements without departing from those principles. The appended claims are therefore intended to cover and embrace any such modifications within the limits only of the true spirit and scope of the invention.

What I claim is:

1. Locking apparatus for a capsule to be used for internal consumption, comprising, in combination:

(a) a hollow first section having an open end and a closed end;

(b) a hollow second section having an open end and a closed end and mateable at the open end thereof with the first section at the open end thereof to form an enclosure; and (c) latching means associated with the first section and with the second section for locking the first section to the second section, the latching means including a projecting member provided on the first section and an abutment provided on the second section and arranged for lockingly engaging the projecting member, the projecting member comprising an annular flange, and the abutment being arranged extending inwardly of the second section and cooperatively interengageable with the annular flange to form locking means for permitting the first section and the second section to be separated only by forces at least partially destructive of at least the first section; and (d) wherein the annular flange comprising a recessed portion extending toward the open end of the first section and offset inwardly of the first member, and terminating in an open one-half of a torus forming an annular facing the closed end of the first section, with the abutment comprising an anchor ring extending inwardly from an outer surface of the second section and opening toward the closed end of the second section, and being arranged for lockingly engaging with the one-half of a torus of the projecting member, the outer surface of each of the first section and the second section being cylindrical and of substantially equal diameters for matingly engaging one another.

2. Apparatus as defined in claim 1, wherein the annular flange comprises a recessed portion extending inwardly toward the open end of the first section and arranged medially thereof, and terminating in an open one-half of a torus forming an annulus facing the closed end of the first section.

3. Apparatus as defined in claim 2, wherein the abutment comprises an anchor ring extending inwardly from an outer surface of the second section and opening toward the closed end of the second section, and being arranged for lockingly engaging with the one-half of the torus of the projecting member, the outer surface of each of the first section and second section being cylindrical and of substantially equal diameters for matingly engaging one another.

4. An improvement as defined in claim 3, wherein the projecting member is spaced from the open end of the first section, and a sleeve being provided in the first section between the projecting member and the open end of the first section, the sleeve being penetratable into the second section at the open end thereof a sufficient predetermined distance to provide a junction between the first section and the second section which resists bending and like movements.

5. Apparatus as defined in claim 1, wherein the abutment comprises an anchor ring arranged extending inwardly from an outer surface of the second section, and being arranged for lockingly engaging with the projecting member, each of the abutment and the projecting member having a cross section similar to the other and arranged for matingly engaging with one another, the first section being longer than the second section and having a flared open end arranged for facilitating guiding of the first section into the second section, the cross section of at least one of the abutment and projecting member generally being of a saw-tooth configuration.

6. Apparatus as defined in claim 5, wherein there are a plurality of abutments and cooperating projecting members arranged side-by-side on a respective one of the first section and the second section.

7. An improvement as defined in claim 5, wherein the projecting member is spaced from the open end of the first section, and a sleeve being provided in the first section between the projecting member and the open end of the first section, the sleeve being penetratable into the second section at the open end thereof a sufficient predetermined distance to provide a junction between the first section and the second section which resists bending and like movements.

8. In an edible capsule including a first section and a second section, each section comprising a generally cylindrical, hollow body having a pair of spaced ends, one of the ends being closed and the other of the ends being open, each section being joinable to the other section at the open end thereof to form an enclosure, the improvement comprising latching means associated with the first section and with the second section for locking the first section to the second section and permitting separation of the first section and the section only by forces at least partially destructive of at least one of the first section and the second section, the latching means including a projecting member provided on the first section, and an abutment provided on the second section and arranged for lockingly engaging the projecting member, the projecting member comprising an annular flange and the abutment being arranged extending inwardly of the second section and cooperatively interengageable with the annular flange wherein the annular flange comprises a recessed portion extending toward the open end of the first section and offset inwardly of the first member, and terminating in an open one-half of a torus forming an annulus facing the closed end of the first section, with the abutment comprising an anchor ring extending inwardly from an outer surface of the second section of opening toward the closed end of the second section, and being arranged for lockingly engaging with the one-half of a torus of the projecting member, the outer surface of each of the first section and the second section being cylindrical and of substantially equal diameters for matingly engaging one another.

9. An improvement as defined in claim 8, wherein the abutment comprises an anchor ring extending inwardly from an outer surface of the second section, and is arranged for lockingly engaging with the projecting member, each of the abutment and the projecting member having a cross section similar to the other and arranged for matingly engaging one another.

10. An improvement as defined in claim 9, wherein the cross section of at least one of the abutment and the projecting member generally is of a saw-tooth configuration.

11. An improvement as defined in claim 9, wherein there are a plurality of abutments and cooperating projecting members arranged side-by-side on respective ones of the first section and the second section.

12. An improvement as defined in claim 11, wherein the cross section of each of the abutment and the projecting member generally is of a saw-tooth configuration.

13. An improvement as defined in claim 9, wherein the projecting member is spaced from the open end of the first section, and a sleeve being provided in the first section between the projecting member and the open end of the first section, the sleeve being penetratable into the second section at the open end thereof a sufficient predetermined distance to provide a junction between the first section and the second section which resists bending and like movements.

14. An improvement as defined in claim 8, wherein the projecting member is spaced from the open end of the first section, and a sleeve being provided in the first section between the projecting member and the open end of the first section, the sleeve being penetratable into the second section at the open end thereof a sufficient predetermined distance to provide a junction between the first section and the second section which resists bending and like movements.

* * * * *